US009861345B2

(12) United States Patent
Cao et al.

(10) Patent No.: US 9,861,345 B2
(45) Date of Patent: Jan. 9, 2018

(54) SKIN TISSUE BIOPSY DEVICE

(71) Applicant: THE REGENTS OF THE UNIVERSITY OF MICHIGAN, Ann Arbor, MI (US)

(72) Inventors: Ke Cao, Shanghai (CN); Grace Xiang Gu, Orchard Lake, MI (US); Yang Xu, Taizhou (CN); Yuchen Hua, Shanghai (CN); Shorya Awtar, Ann Arbor, MI (US); Joshua Bishop-Moser, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 61 days.

(21) Appl. No.: 14/391,284

(22) PCT Filed: Apr. 11, 2013

(86) PCT No.: PCT/US2013/036136
§ 371 (c)(1),
(2) Date: Oct. 8, 2014

(87) PCT Pub. No.: WO2013/155278
PCT Pub. Date: Oct. 17, 2013

(65) Prior Publication Data
US 2015/0073300 A1    Mar. 12, 2015

Related U.S. Application Data

(60) Provisional application No. 61/622,628, filed on Apr. 11, 2012.

(51) Int. Cl.
A61B 10/02        (2006.01)
A61B 17/3205      (2006.01)

(52) U.S. Cl.
CPC .... A61B 10/0266 (2013.01); A61B 17/32053 (2013.01); A61B 2010/0208 (2013.01)

(58) Field of Classification Search
CPC ................... A61B 10/0266; A61B 2010/0208
See application file for complete search history.

(56) References Cited

U.S. PATENT DOCUMENTS 4,699,154 A * 10/1987 Lindgren ........... A61B 10/0275
                                                    600/567
4,944,308 A *  7/1990 .ANG.kerfeldt ... A61B 10/0275
                                                    600/564

(Continued)

FOREIGN PATENT DOCUMENTS

WO    WO 0224077 A1 *  3/2002  ......... A61B 10/0275
WO    WO-0224077 A1    3/2002

OTHER PUBLICATIONS

International Search Report and Written Opinion for PCT/US2013/036136, dated Jul. 25, 2013; ISA/KR.

Primary Examiner — Michael C Stout
Assistant Examiner — Nicholas E Kolderman
(74) Attorney, Agent, or Firm — Harness, Dickey & Pierce, P.L.C.

(57) ABSTRACT

A tissue biopsy device comprising an inner needle loaded by a first spring and held in place by a first trigger; an outer needle loaded by a second spring and held in place by a second trigger; an outer housing that surrounds the first and the second needles; and a handle attached thereto.

10 Claims, 10 Drawing Sheets

(56) References Cited

U.S. PATENT DOCUMENTS

| | | |
|---|---|---|
| 4,953,558 A | 9/1990 | Akerfeldt |
| 5,368,045 A | 11/1994 | Clement et al. |
| 5,842,999 A | 12/1998 | Pruitt et al. |
| 6,358,217 B1 * | 3/2002 | Bourassa ........... A61B 10/0275 600/567 |

* cited by examiner

State 1    State 2    State 3

SKIN TISSUE BIOPSY DEVICE

CROSS-REFERENCE TO RELATED APPLICATIONS

This application claims the benefit of U.S. Provisional Application No. 61/622,628, filed on Apr. 11, 2012. The entire disclosure of the above application is incorporated herein by reference.

FIELD

The present disclosure relates to biopsy devices and, more particularly, to a skin tissue biopsy device.

BACKGROUND AND SUMMARY

This section provides background information related to the present disclosure which is not necessarily prior art. This section provides a general summary of the disclosure, and is not a comprehensive disclosure of its full scope or all of its features.

Skin tissue biopsies are commonly used to extract skin from a person's body to either study for research or for clinical diagnostic purposes. The present teachings provide a skin tissue biopsy device that can extract a piece of skin with minimum pain and store it for research and disease diagnosis. Separate from the new tissue biopsy device, the present teachings further provide a tissue storage and transportation device. The two devices can be used in combination for any skin biopsy application that requires a relatively fast procedure, minimum pain, ease of performance, and minimum invasiveness. These applications include tests for any markers for diseases such as osteoporosis, skin cancers or other skin diseases. The present teachings provide a device that contains an outer housing, two latch components, inner needle, and an outer needle. The present disclosure provides a description of the design of the components and assembly thereof.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
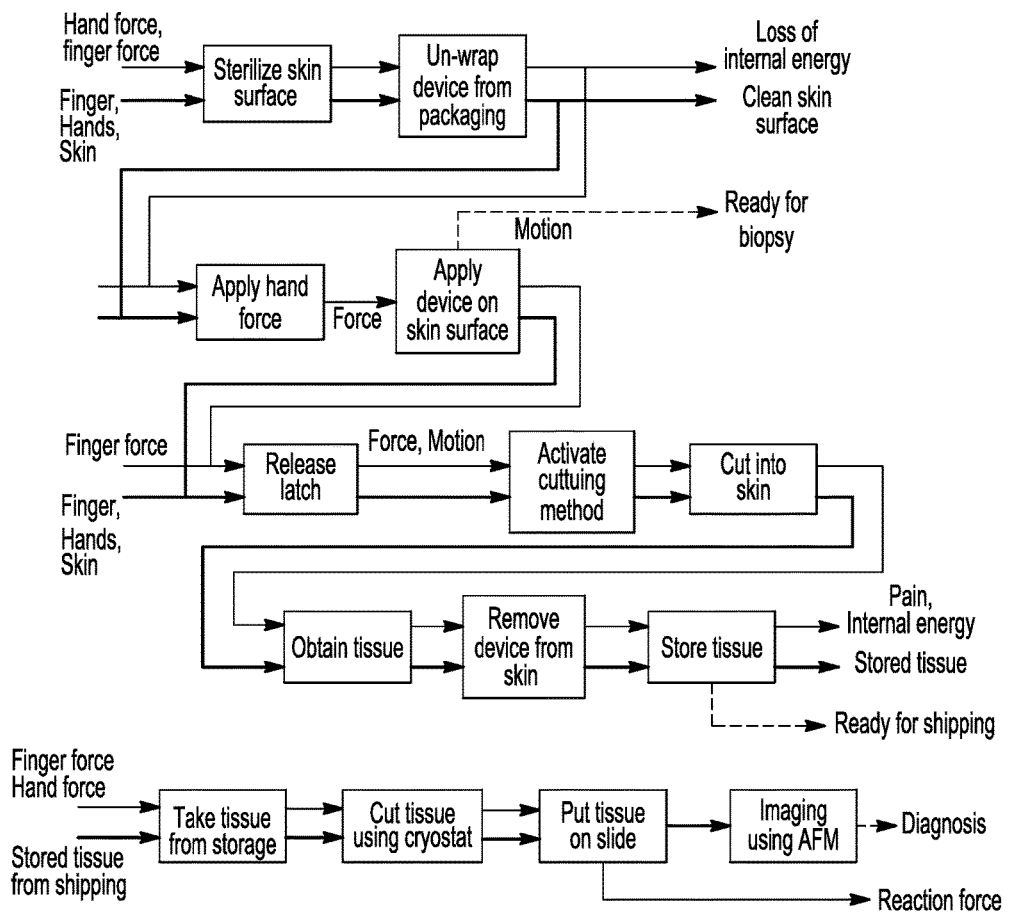
FIG. 1 is a flowchart illustrating a function decomposition of tissue biopsy procedures.

Example embodiments will now be described more fully with reference to the accompanying drawings. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

With particular reference to the present teachings, the design requirements can be determined according to customer needs. Generally, the skin biopsy device of the present teachings has four different potential customers. These include the patients who need skin biopsy for diagnosis of different diseases, such as osteoporosis; the physician who will perform the skin biopsy procedure to obtain or otherwise extract sample tissue; the insurance company who will pay for the skin biopsy; and the technician who will analyze the tissue sample.

Different customers have different requirements in connection with skin biopsy devices. Specifically, patients typically require minimum invasiveness and minimum pain during the skin biopsy process. The physicians require that the procedure of obtaining sample tissue be simple and fast, and the device be reliable and present low risks of complications. The insurance companies require that the device have a low cost and improve the patient outcomes at the same time. The technicians require that the sample tissue is taken from the dermal layer of the skin and the handling of the extracted sample is minimized before imaging. In many cases, it is necessary to ship the tissue sample from physician to technician; therefore it is desirable to store the sample tissue for 3-4 days.

Engineering specifications corresponding to each customer requirement can be assembled. To this end, it was determined that to minimize the pain that the patient feels, the pain of any procedure associated with the present biopsy device should be compared to a simple needle injection of gage 24 and should require no anesthesia and stitches. To minimize the invasiveness, it was determined that the cut diameter should be between about 0.5 to about 1 mm— because a diameter larger than 1 mm will cause much pain and less than 0.5 mm may not be sufficient to obtain a useful sample. The cut depth should be around about 3 mm, because of the depth of dermal layer at the sample location.

To make the skin biopsy easy and fast to perform, it was determined that the steps necessary to take the sample tissue would be to 4 to 7 and takes less than about 5 minutes. This time duration was chosen because the procedure requires sterilization, sampling, and storing and a duration greater than about 5 minutes may compromise sample quality. To achieve the reliability of the procedure, the device should be able to extract tissue sample from skin. To minimize the manufacture cost, the skin biopsy device should be less than 20 US dollars. To ship the sample tissue from physician to technician, the device should store the sample tissue and maintain the nano-scale structure of the tissue for more than 72 hours, which is enough for overnight mail. To help the technician for imaging, it is desirable to easily separate tissue from the device. To minimize the handling of the sample tissue, the handling by the technician should be limited to about 3-5 times before viewing, such as separating the tissue sample, cutting the tissue sample and set it for imaging. In addition, to meet the medical design regulations, all material should be able to be sterilized. The customer requirements and engineering specification developed are presented in Table 1.

TABLE 1

Customer Requirements and Corresponding Engineering Specifications

| Customer Requirements | Engineering Specifications |
| --- | --- |
| Minimum pain | Pain compared to a simple needle injection |
| Minimum invasiveness | Cut diameter 0.5-1 mm, depth <3 mm |
| Fast to perform | Procedure time <5 min |
| Easy to perform | 4-7 steps for nurse practitioner level |
| Reliability of device | Able to obtain tissue sample from skin |
| Low cost | Manufacture cost <20 US dollars |
| Store tissue for shipping | Maintain nano-scale structure for 3-4 days |
| | Weight <50 g |
| Prepare tissue for imaging | Sample that can be cut to 10 microns by 10 microns to put under AFM |
| | Able to separate the tissue from the device |
| Minimizing handling for imaging | Technician only touches sample 3-5 times before viewing it |

It was determined that the most important requirement is a procedure that is minimally painful. Minimizing the pain of the procedure will increase the adoption rate of the skin biopsy method for diagnosis of different diseases. The second important requirements are reliability, and shipping and storage of the sample tissue as they determine whether technician can analyze the skin sample and find out whether the patient has a certain disease or not. Minimum invasiveness is also important as it is related to the pain the patient feels and the time it takes for the wound to heal. The quality of tissue preparation is important, as a qualified sample is necessary for imaging. Speed and ease of use are secondary considerations, yet remain important for rapid adoption by physicians. Cost is a tertiary concern for the initial device, as subsequent engineering refinement for mass production will lower per device cost.

Concept Generation

Figure 2:
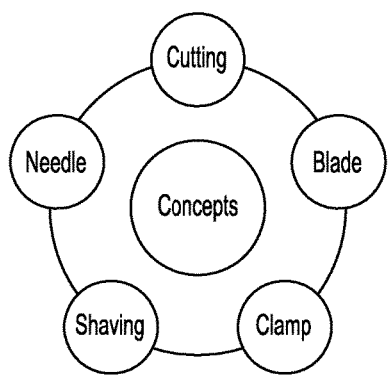
FIG. 2 is a concept tree illustrating alternative design concepts according to some embodiments of the present teachings.

To generate different concepts for the skin biopsy device, a functional decomposition was conducted to decide what fundamental steps the device will take. The functional decomposition diagram is in FIG. 1. Five main concepts for tissue extraction are: cutting, blade, clamp, needle, and shave. The main concepts are shown in the concept tree in FIG. 2. The cutting concept comes from the idea of scissors. The blade concept came from the idea of a knife cutting through skin. The clamp concept came from the idea of grabbing something that closes in on the object. The needle concept came from the idea of drawing blood using needle and also needle biopsies. Lastly, the shave concept came from the idea of a dish style scoop. Each design is evaluated for how they met customer requirements.

Figure 3:
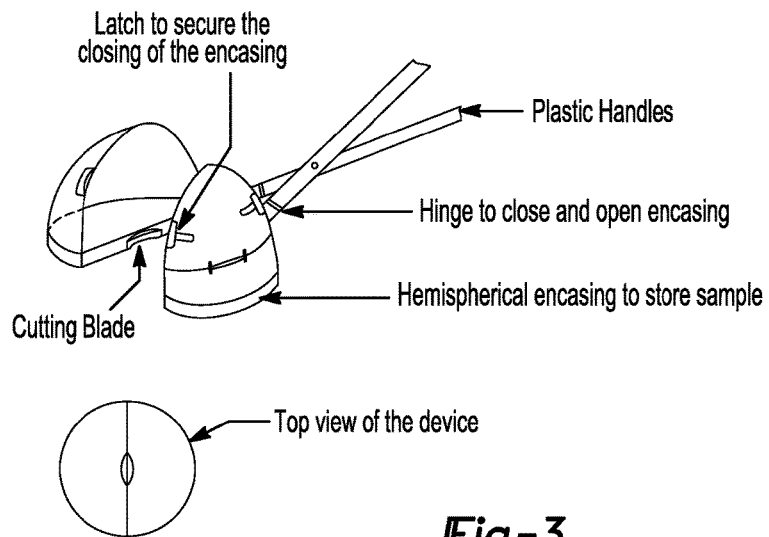
FIG. 3 is a biopsy device according to some embodiments of the present teachings having a cutting, scissor-like design.

Cutting Concept:

As can be seen in FIG. 3, the handles are made of plastic or any other suitable material. A hemispherical encasing space is attached to the cutting blade to protect the sample after it is cut. The cutting blades are indented to enable the device to cut off a circular piece of skin in practice. In practice, the doctor or nurse will hold the scissors by the handles and place the circular part near the desired skin area. The blades are then closed together and a small part of skin will be compressed into the cutting blade area and a small part of tissue will be cut off. Next, the encasing is opened by its hinges and OCT (Optimal Cutting Temperature medium) solution is injected to protect the cut tissue. Then the encasing is closed again and secured by the latch for transportation to a lab.

The advantages and disadvantages of the cutting design are shown in Table 2. The device does not punch into the skin, so the invasiveness is low. Although the cut tissue might contain both epidermis and dermis, the desired tissue from the dermal layer will still be acquired through the standard cryostat process. The major defection of this design is the sealing issue. Even if there is a latch to close the encasing tightly, there might still be some solution leak unless some better sealing methods are applied at the closing edges of the encasing.

TABLE 2

Advantages and disadvantages of cutting design

| Advantages | Disadvantages |
| --- | --- |
| Easy to perform | Not reliable |
| Fast to perform | Not ready for imaging |
| Low invasiveness | Leak |
| Able to store sample | |

Figure 4:
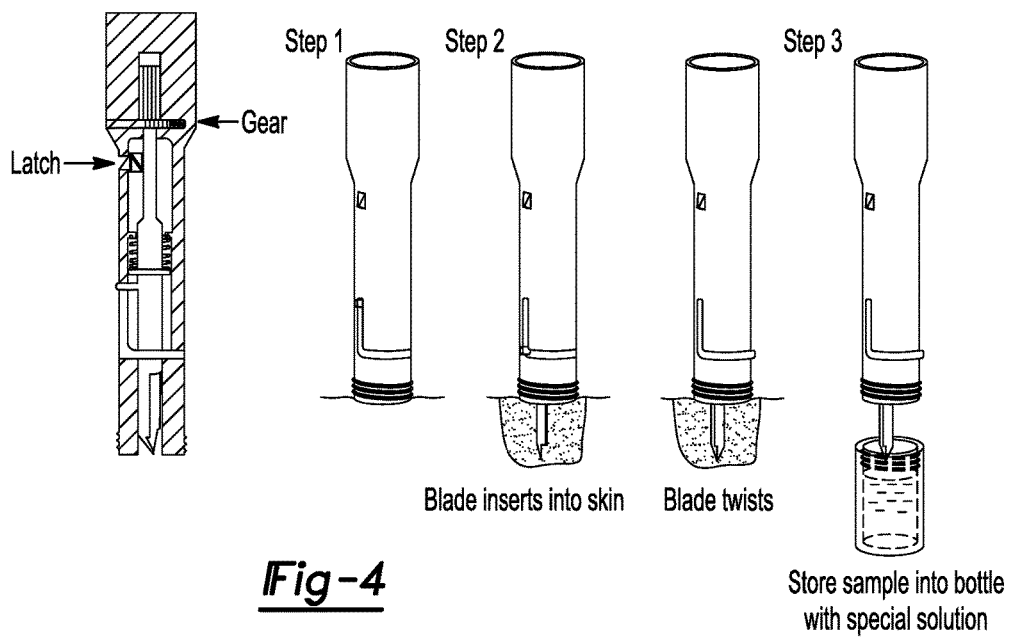
FIG. 4 is a biopsy device according to some embodiments of the present teachings having a rotating blade design.

Blade Concept:

The blade concept is derived from the idea of using the blade to cut off tissue in the dermal layer. As seen in FIG. 4, there are three main components in the design: blade, housing 114, and a sample receptacle assembly 116 with special solution in it. When the latch is pressed, the blade inserts in to the skin. The blade is constrained from turning at first. But after the blade has fully inserted into the skin, it can be turned by a spring loaded gear, which translate linear motion of the gear into rotation of the blade.

In practice, the device is first put on the desired position of the skin sample and the button at the top of the device is pressed. Next, the latched is pressed and the blade will be inserted into the skin. Then the blade will be twisted or rotated to cut an amount of tissue off. Finally, the device is pulled out and screwed into the bottle with OCT.

TABLE 3

Advantages and Disadvantages of Blade Design

| Advantages | Disadvantages |
| --- | --- |
| Fast to perform | Relatively high cost |
| Easy to perform | Reliability is unknown |
| Able to store tissue for shipping | Painful |

Figure 5:
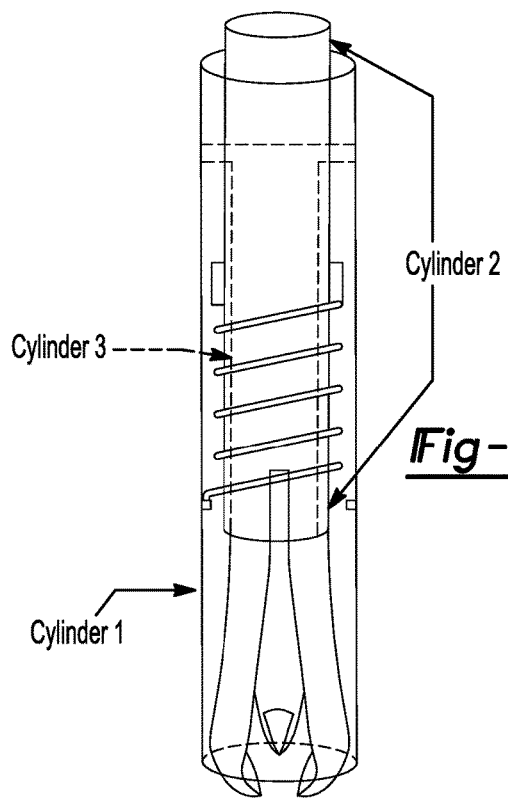
FIG. 5 is a biopsy device according to some embodiments of the present teachings having a multi-cutting prong design.

Clamp Concept:

The idea of clamp comes from the mechanical pencil inner structure. As can be seen in FIG. 5, Cylinder 1 is the main body and is connected with Cylinder 3, which is composed of the dashed lines and the three small blades in FIG. 5. The position of Cylinder 3 can be adjusted to control the cut depth. A spring is attached between Cylinder 1 and Cylinder 2. When Cylinder 2 is kept up by the spring, three blades are open, and when Cylinder 2 is pushed down, the blades will be closed to punch into the skin and take the sample off.

TABLE 4

Advantages and disadvantages of clamp design

| Advantages | Disadvantages |
| --- | --- |
| Low cost | Require training |
| Easy to use | Not reliable |
| Fast to perform | Difficult to separate tissue |
| | Might be painful |
| | Difficult to manufacture |

Figure 6:
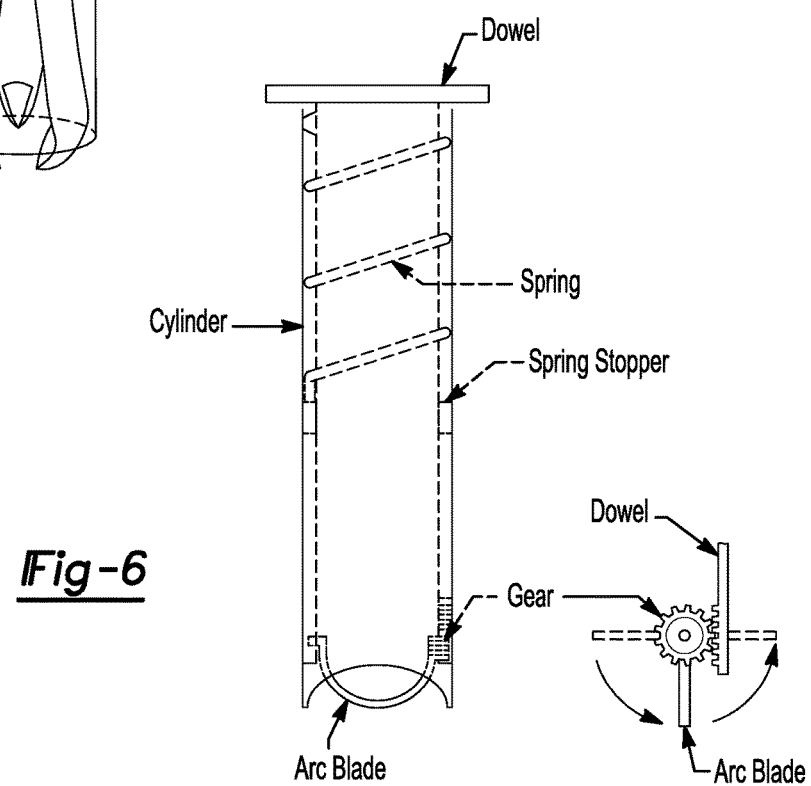
FIG. 6 is a biopsy device according to some embodiments of the present teachings having a cutting, scoop design.
Figure 7:
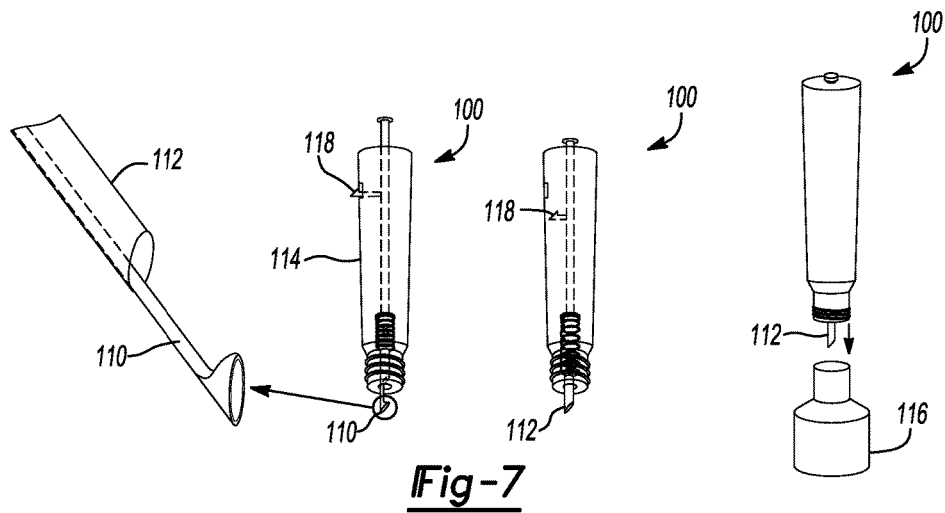
FIG. 7 is a biopsy device according to some embodiments of the present invention having a multi-needle design.

Shave Concept:

The idea of shave concept comes from a kitchen utensil, the dish style scoop. As shown in FIG. 6, the dowel cylinder inserts into and out of the hollow cylinder just like the way a syringe works. The spring connects the outer end of the dowel and the inner stopper attached to the inner wall of the cylinder. The end of the dowel is carved with gear teeth meshing with the gear, to which an arc blade is welded with the same rotation axis. As the dowel is inserted into the cylinder, the gear is driven and the arc blade is rotated by around 180°, cutting a piece of tissue off. Then the dowel is released and repulsed by the spring and the arc blade is rotated in the opposite direction by 180° back to the original position.

The advantage of this design is the whole process of cutting off the tissue is fast and easy. The invasiveness is also small because the arc edge of the end of the cylinder enables the arc blade to obtain the sample at the same horizontal level of the cylinder end. However, the whole biopsy process includes punching and rotating and the patient may feel pain. In addition, since the mechanism is complicated and the device is supposed to be as small as possible, it will be very difficult to fabricate the small parts.

TABLE 5

Advantages and disadvantages of shave design

| Advantages | Disadvantages |
| --- | --- |
| Low invasiveness | Painful |
| Fast to perform | Difficult to store and handle for imaging |
| Easy to perform | Difficult to fabricate |

Needle Concept:

This design is inspired by the biopsy needle. As shown in FIGS. 7-19, biopsy device 100 of the present teachings comprises an inner needle 110, an outer needle 112, a shell or housing 114, and an optional and separate sample receptacle assembly 116 having a predetermined biopsy solution contained therein. In some embodiments, inner needle 110 can be fixed while outer needle 112 is spring loaded and operable to move relative to inner needle 110 to achieve a cutting and containing operation. Outer needle 112 can be triggered by a latch mechanism 118 disposed on housing 114 and operated by a user.

The general procedure of operating biopsy device 100, in some embodiments, is described below. At step 1, inner needle 110 is inserted into the skin surface and an upper or first trigger latch 120 of latch mechanism 118 is pressed. At step 2, as deployment of inner needle 110 triggers outer needle 112 (via a second trigger latch 122), outer needle 112 will cut into the skin and obtain the skin sample. At step 3, biopsy device 100 is pulled out and screwed or placed into sample receptacle assembly 116 with special solution.

TABLE 6

Advantages and disadvantages of needle

| Advantage | Disadvantage |
| --- | --- |
| Minimum pain | Relatively high cost |
| Minimum invasiveness | Reliability is unknown |
| Fast to perform | |
| Easy to perform | |
| Able to store tissue for shipping | |

Concept Comparison

With the cutting, blade, clamp, shave and needle concept given, we generated a Pugh Chart according to the customer requirements, as shown in Table 7. Minimum pain for patient, reliability of obtaining desired sample and the tissue shipping and imaging are considered the most valuable and give them the highest weights. From the Pugh Chart, the biopsy needle concept is seen as the best idea with highest rating and is further refined.

The invention and its minor variations are described below.

Figure 8:
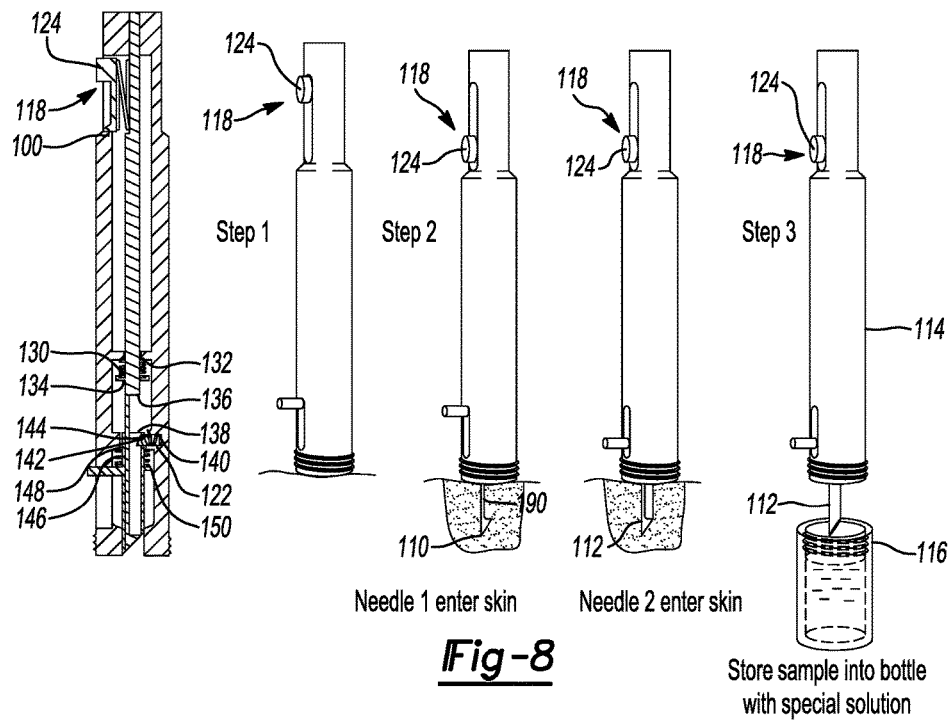
FIG. 8 is the biopsy device according to some embodiments of the present teachings.
Figure 11:
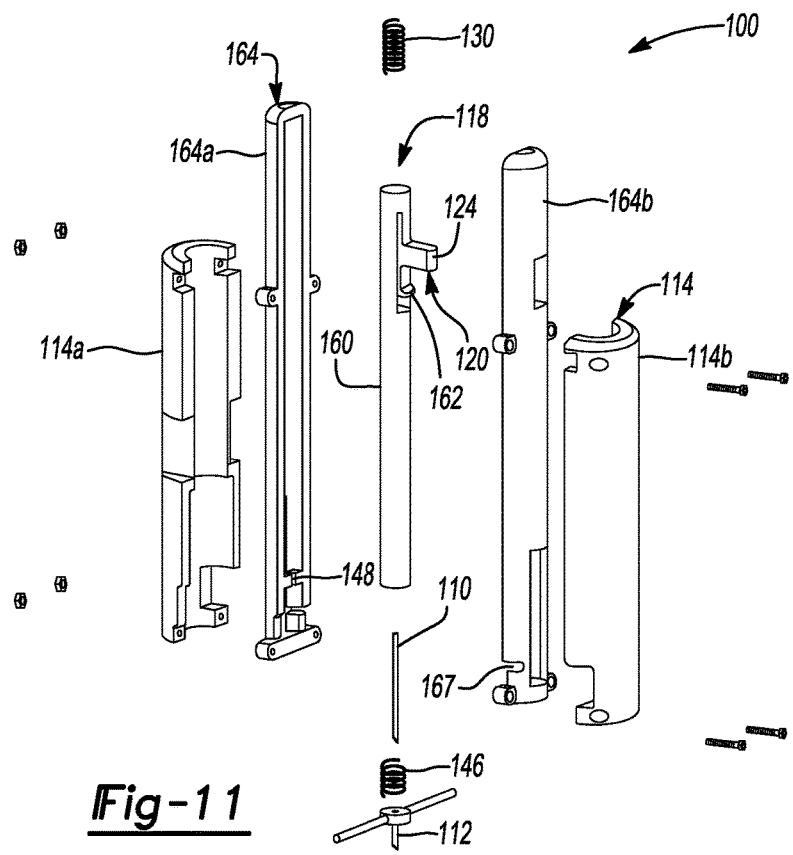
FIG. 11 is an exploded perspective view of the tissue biopsy device according to principles of the present teachings.

This design is inspired by a standard biopsy needle, but contains several improvement not found in the prior art. As shown in FIG. 8, there are four main components in the design: inner needle 110, outer needle 112, housing 114, and an optional and separate sample receptacle assembly 116 with special solution in it. Both inner needle 110 and outer needle 112 are spring loaded. Inner needle 110 can be triggered by upper trigger latch 120 of latch mechanism 118 and outer needle 112 can be triggered by lower trigger latch 122 of latch mechanism 118 when inner needle 110 contacts lower trigger latch 122 of latch mechanism 118. In some embodiments, upper trigger latch 120 can comprise an elongated flexural member or living hinge to permit articulation and elastic movement thereof. In other words, the elongated flexural member or living hinge of upper trigger latch 120 can comprise a localized flexure joint along a beam member. In some embodiments, upper trigger latch 120 can be formed as a monolithic or unitary member associated with surrounding structure, such as the inner cylinder 160 (FIG. 11). Specifically, in some embodiments, upper trigger latch 120 can comprise a monolithically/unitary formed elongated beam having a distal latch end 162 for engaging associate latching structure formed on adjacent housing or inner cylinder 164b that is capable of elastic deformation. The elongated beam can comprise a protruding button 124 for actuation by a user.

TABLE 7

Pugh Chart for different concept designs

| Customer Requirements | Weights | Cutting | Blade | Clamp | Shaving | Needle | Total |
| --- | --- | --- | --- | --- | --- | --- | --- |
| Minimum pain | 9 | 3 | 3 | 3 | 3 | 4 | 5 |
| Minimum invasiveness | 7 | 4 | 3 | 4 | 4 | 4 | 5 |
| Fast to perform | 3 | 4 | 3 | 4 | 3 | 4 | 5 |
| Easy to perform | 4 | 2 | 3 | 3 | 3 | 4 | 5 |
| Reliability of obtaining sample | 8 | 4 | 4 | 3 | 4 | 4 | 5 |
| Able to be sterilized | 4 | 4 | 4 | 2 | 2 | 4 | 5 |
| Low cost | 2 | 4 | 4 | 4 | 2 | 4 | 5 |
| Store tissue for shipping | 8 | 2 | 4 | 3 | 2 | 4 | 5 |
| Prepare tissue for imaging | 7 | 2 | 4 | 3 | 2 | 4 | 5 |
| Minimizing handling for imaging | 6 | 2 | 3 | 3 | 2 | 3 | 5 |
| | | 58 | 59.6 | 70 | 62.6 | 56 | 78 | 100 |

The procedure of operating biopsy device 100 is described below. At step 1, biopsy device 100 is placed in direct contact on the patient's skin in a position where the biopsy is to be taken and upper trigger latch 120 is actuated via a button 124 by the healthcare provider. At step 2, as the button 124 triggers inner needle 110, inner needle 110 is propelled into the skin in response to spring force. The spring force is a product of compression of first extension spring 130 compressed between an inner flange 132 of housing 114 and an outer flange 134 of inner needle 110. During this process, inner needle 110 will contact lower trigger latch 122 of latch mechanism 118 and consequently and automatically trigger outer needle 112—this can be timed such that it occurs once inner needle 110 has deployed a predetermined distance into the patient's tissue (e.g. fully deployed, partially deployed). Specifically, a notch 136 formed in the shank of inner needle 110 contacts a top surface 138 of outer needle 112 thereby overcoming lower trigger latch 122. It should be appreciated that a biasing force of lower trigger latch 122 must be less than the force caused by contact of the deploying inner needle 110 to outer needle 112. Lower trigger latch 122 can comprise a biased member 140 slidably received within a retention notch 142 formed in outer needle 112. In some embodiments, retention notch 142 can comprise a sloped surface 144 to encourage disengagement of lower trigger latch 122 from outer needle 112 upon contact of notch 136 of inner needle 110 with top surface 138 of outer needle 112. Thereafter, outer needle 112 will be disengaged from lower trigger latch 122 and outer needle 112 is propelled into the skin in response to spring force. Outer needle 112 includes a sharpened distal tip operable for cutting tissue surrounding inner needle 110 and retaining a portion thereof between outer needle 112 and inner needle 110. The spring force is a product of compression of a second extension spring 146 compressed between an inner flange 148 of housing 114 and an outer flange 150 of outer needle 112. At step 3, biopsy device 100 is pulled out of the skin and screwed into sample receptacle assembly 116 with special solution.

Figure 9:
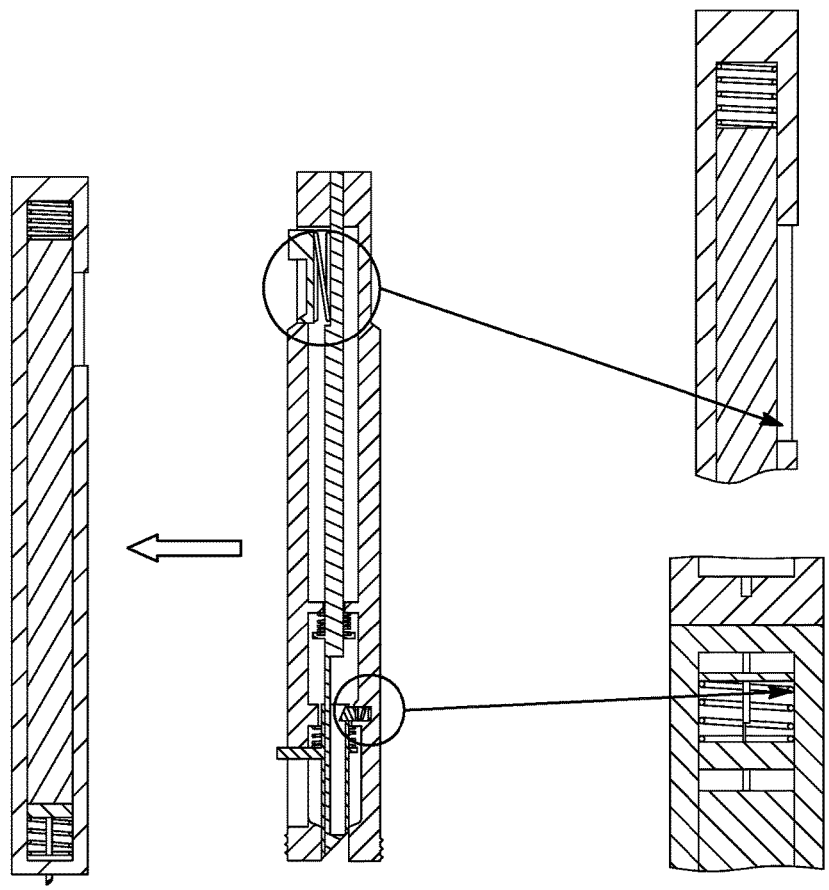
FIG. 9 is a representative computer aided design (CAD) according to some embodiments of the present teachings.

A SolidWorks model was created relating to the present invention. FIG. 9 illustrates how the CAD model is related to the drawing. The specific CAD drawing of the latches are shown in the later sections.

Figure 10:
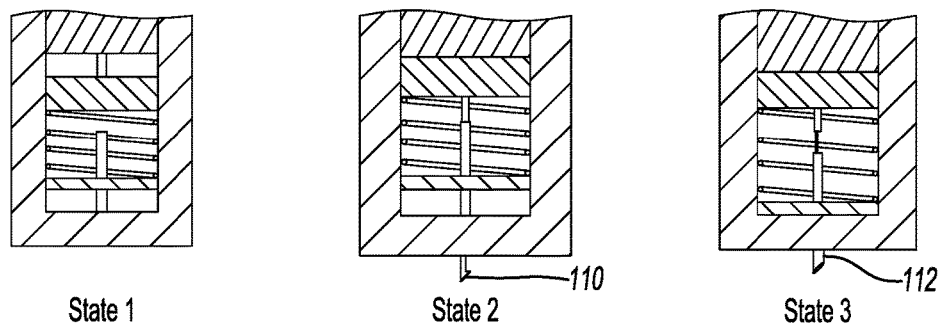
FIG. 10 is a series of representative CAD images illustrating various deployment states of the present teachings.

Three specific states of biopsy device 100 are shown in FIG. 10. State 1 is the start state at which first extension spring 130 and second extension spring 146 are compressed. When a user actuates latch mechanism 118 via button 124, the first extension spring 130 will be released and accelerate inner needle 110 downward and will be pushed into skin as shown in State 2. When inner needle 110 or associated structure contacts a physical stop, such as outer flange 134 of inner needle 110 and inner flange 148 of housing 114, lower trigger latch 122 is released as described herein. Outer needle 112 will be pushed into skin as shown in State 3. At this stage, the skin sample will stay between inner and outer needles 110 and 112 respectively.

Figure 13:
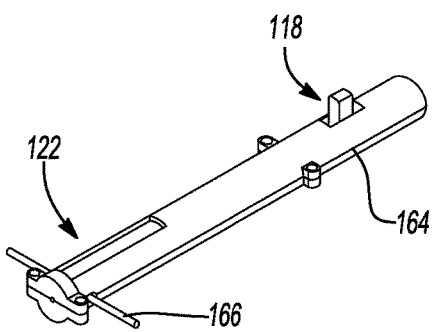
FIG. 13 is a perspective view of the inner cylinder of the tissue biopsy device according to principles of the present teachings.
Figure 14:
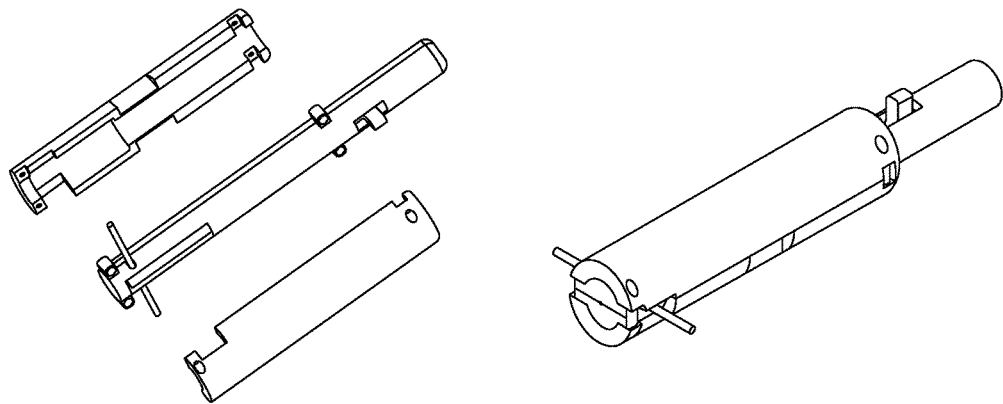
FIG. 14 is a perspective view of the outer housing of the tissue biopsy device according to principles of the present teachings.
Figure 15:
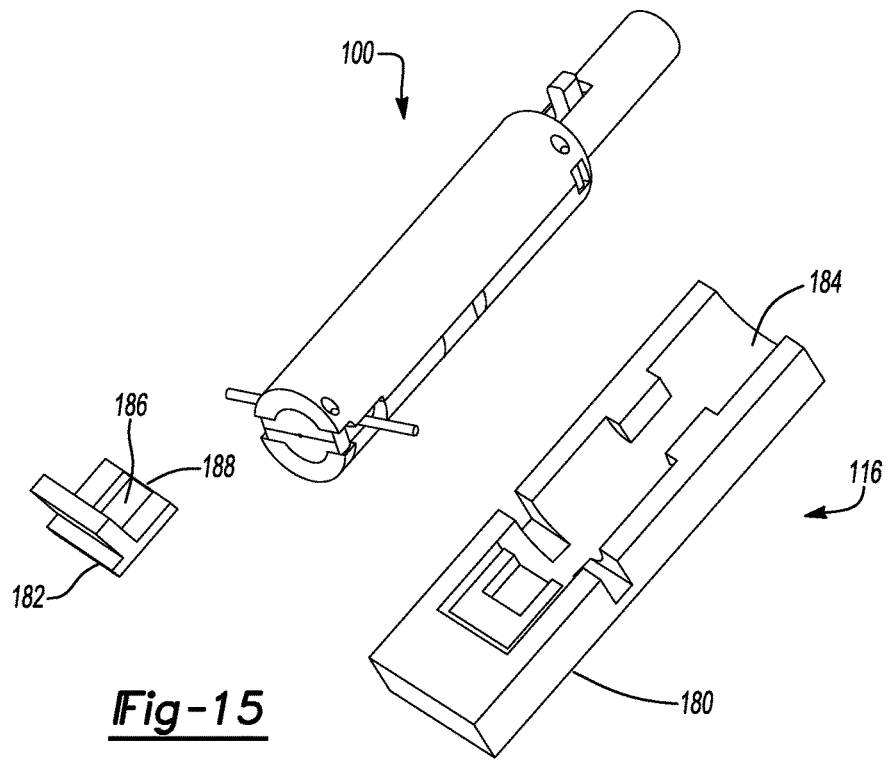
FIG. 15 is a perspective view of the sample receptacle according to principles of the present teachings.
Figure 16:
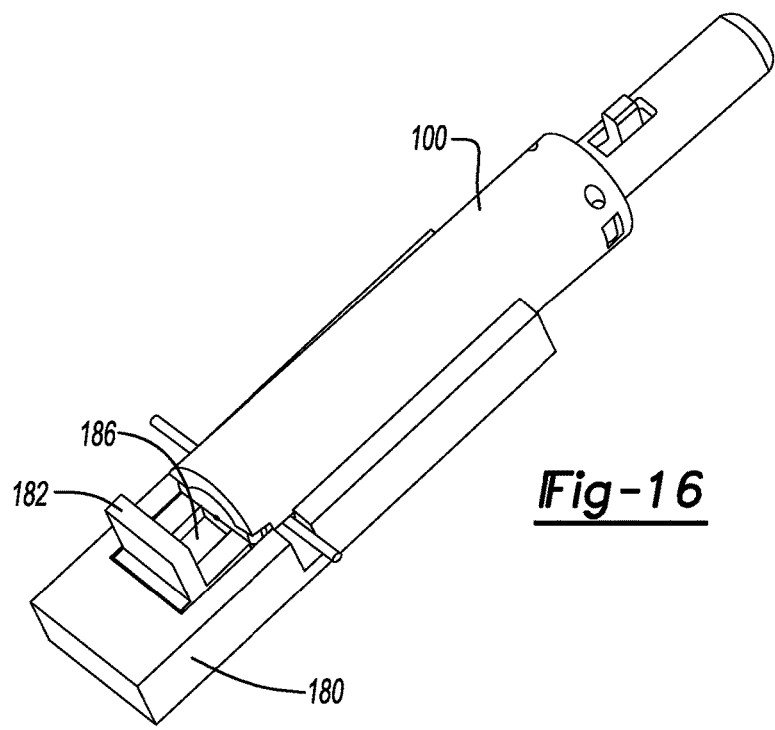
FIG. 16 is a perspective view of the sample receptacle and the tissue biopsy device according to principles of the present teachings.
Figure 17:
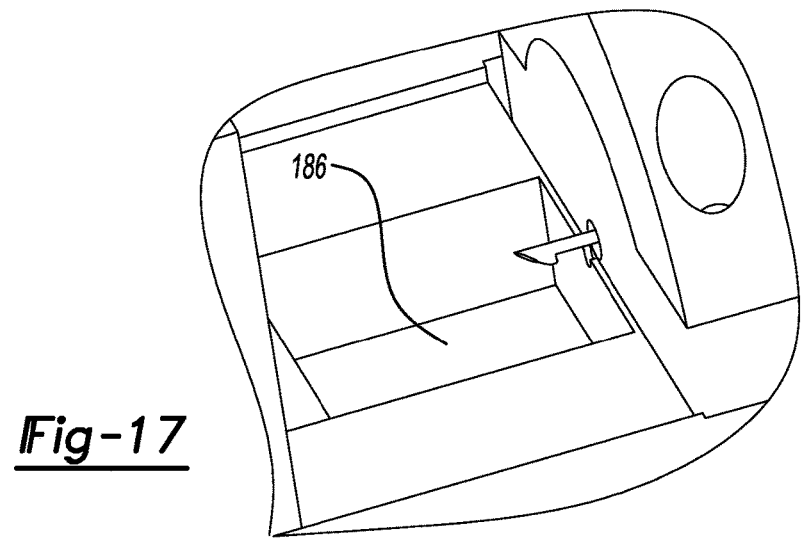
FIG. 17 is an enlarged perspective view of the sample receptacle and the tissue biopsy device according to principles of the present teachings.

After refining the present design, detailed CAD drawings of the assembly were developed as illustrated in FIGS. 11-14 shows the detailed assembly of the biopsy part and FIGS. 15-17 illustrate the interface of biopsy device 100 and sample receptacle assembly 116.

Biopsy Device 100

With particular reference to FIGS. 11-14, in some embodiments, biopsy device 100 can comprise a multi-piece housing and cylinder assembly to provide a robust and reliable construction and operation. Specifically, biopsy device 100 can comprise inner needle 110 being coupled to an inner cylinder 160 for movement therewith. Inner cylinder 160 can comprise upper trigger latch 120, including button 124 and a latch end 162. Inner cylinder 160 can be generally tubular in shape.

Figure 12:
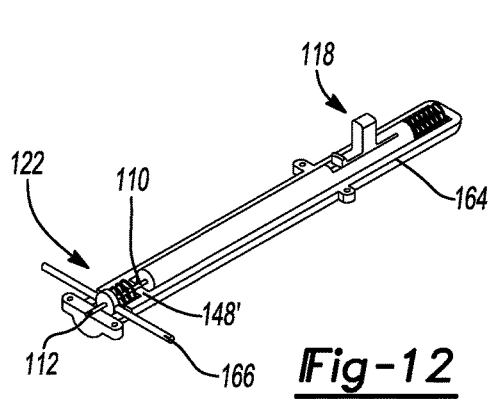
FIG. 12 is a perspective view of the tissue biopsy device according to principles of the present teachings having portions removed for clarity.

Inner cylinder 160 can be slidably disposed within an inner housing 164 having opposing housing halves 164a and 164b. Halves 164a and 164b each include an inner volume that is sized and shaped to slidably receive inner cylinder 160, as illustrated in FIGS. 12 and 13, and the halves can be joined together via fasteners. In this embodiment, first extension spring 130 can be disposed between a top surface of inner cylinder 160 and an inner top wall of inner housing 164, thereby exerting a biasing force therebetween. Similarly, second extension spring 146 can be disposed between inner flange 148' of inner housing 164 and outer flange 150 of outer needle 112, thereby exerting a biasing force therebetween.

Inner needle 110 passes through the second extension spring 146 and the hollow outer needle 112.

Outer housing 114 can comprise halves 114a and 114b. Halves 114a and 114b each include an inner volume that is sized and shaped to slidably receive inner housing 164, as illustrated in FIG. 14, and the halves can be joined together via fasteners. Outer housing 114 is sized to be grasped by a healthcare provider during deployment of inner needle 110 and outer needle 112.

When the button on the upper trigger latch 120 is pressed, the upper trigger latch 120 will bend and hence release inner needle 110. Inner needle 110 will then insert into the skin. As inner needle 110 goes down, the cylinder connected to inner needle 110 will touch the bumps of the lower trigger latch 122 and push the lower trigger latch 122 away, the lower part of the lower trigger latch 122 will then release outer needle 112 and outer needle 112 will cut through the skin and obtain a skin sample between the inner and outer needle. After obtaining the skin sample, the whole device will be pulled out. Then by pulling the handle or release member 166 connected to outer needle 112 up and rotating handle 166 into a retaining slot 167 formed in housing 164, outer needle 112 will be pulled up and expose the skin sample held by inner needle 110. Biopsy device 100 can then be interfaced with the storage device to store the tissue for shipping or handling.

Sample Receptacle Assembly 116

Sample receptacle assembly 116 is composed of two parts: The plastic base 180 and the plastic mold 182. The plastic base 180 has inward bumps 184 that fit the shape of the outer housing 114 of biopsy device 100 and fixes or retains biopsy device 100 tightly. The plastic mold 182 has a basin 186 for injecting OCT, and a small groove 188 is left on the edge of the thin wall to hold inner needle 110. When inner needle 110 is put on the mold with OCT solution, the notch 190 (FIG. 8) formed in inner needle 110 holding the tissue is faced downwards to let the tissue be exposed to OCT. Then, according to a standard tissue storage process, the whole device is put into an aluminum box filled with dry ice and is frozen for storage and shipping. When biopsy device 100 is taken out, the extraction device is removed, with the tissue left in the OCT plate.

For purposes of exemplary construction, the following dimensions are provided. However, it should be understood that variations in both size and shape are anticipated by the present disclosure.

Upper Trigger Latch 120

Figure 18:
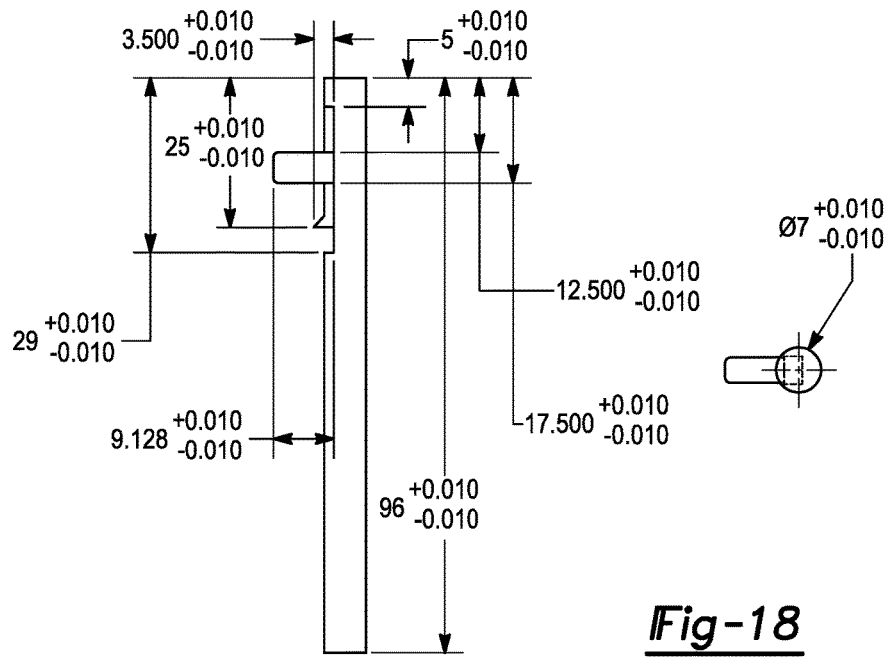
FIG. 18 is a detailed view of the upper latch of the biopsy tissue device according to principles of the present teachings.
Figure 19:
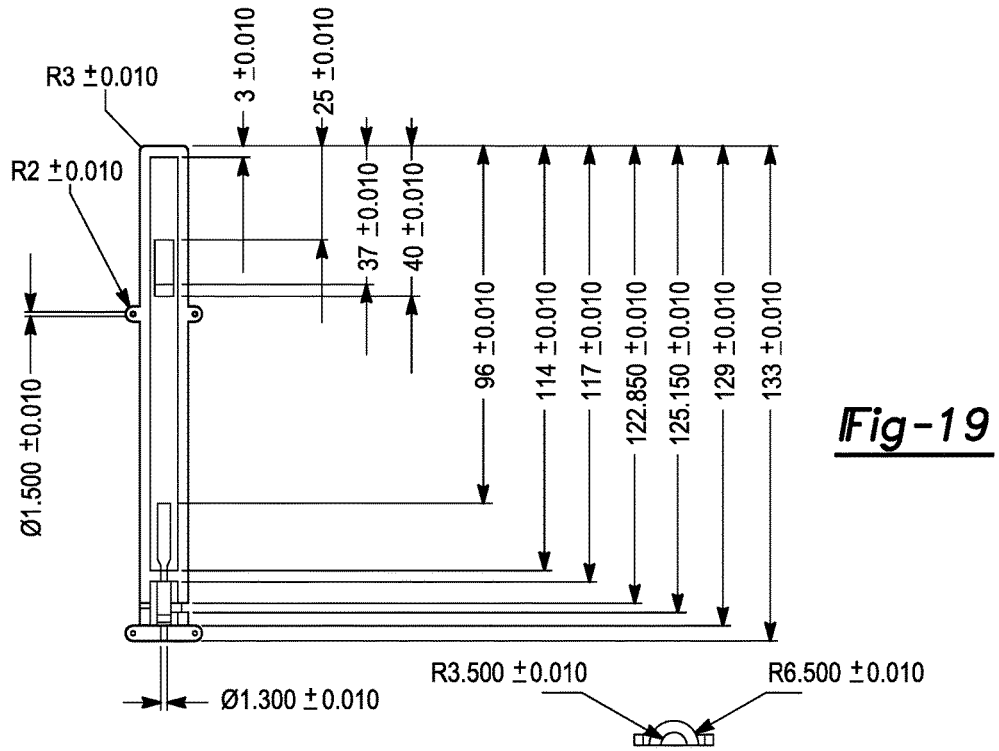
FIG. 19 is a detailed view of the lower latch of the biopsy tissue device according to principles of the present teachings.

The dimension of the upper trigger latch 120 is shown in FIG. 18. The width of the latch is 4 mm, the thickness of the latch is 1.5 mm, and the length of the latch is 25 mm. The button is in the middle of the latch. If the button is pressed, the flexural structure of the latch will bend inside. The lower part of the latch will no longer be held by the inner housing and therefore it will release the whole cylinder connected with latch and also inner needle 110 connected to the cylinder. We make the thickness of the latch as small as 1.5 mm so that the maximum stress the upper trigger latch 120 will experience is smaller than the plastic's yield stress and the latch is still safe from buckling.

Lower Trigger Latch 122

The dimension of the lower trigger latch 122 is shown in FIG. 10. The thickness of the latch is 1.6 mm and the length of the latch is 32 mm. The two bumps are located 18 mm from the upper end of the latch. When inner needle 110 goes down, the cylinder connected to the needle will push the bumps of the lower trigger latch 122. The lower trigger latch 122 will then be bent to the outside. When inner needle 110 stops, the lower trigger latch 122 will then be completely pushed aside and release outer needle 112. To make the maximum stress the lower trigger latch 122 experience smaller than the yield stress of plastic and make the lower trigger latch 122 safe from yield caused by tensile force, the thickness of the latch is chosen to be 1.6 mm.

Inner Needle 110

Figure 20:
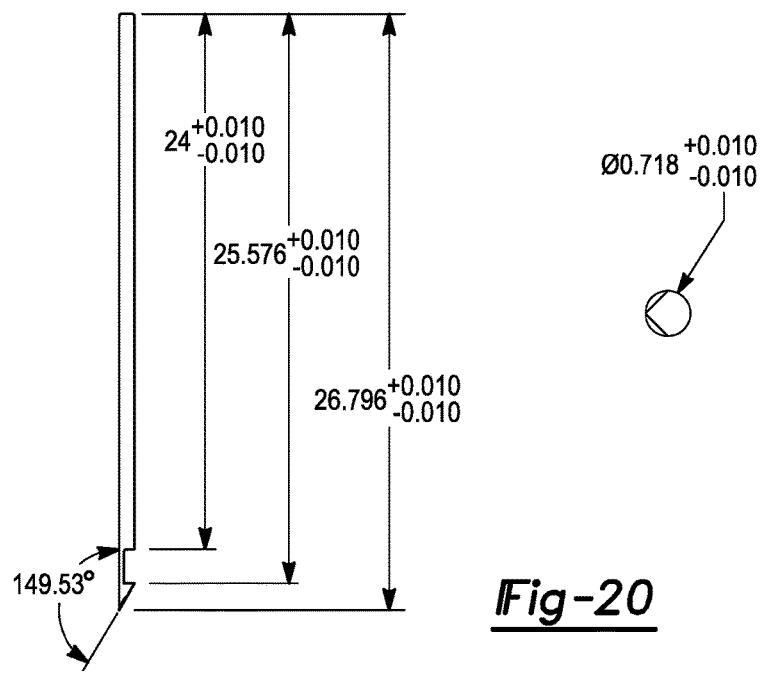
FIG. 20 is a detailed view of the inner needle of the biopsy tissue device according to principles of the present teachings.

The dimension of inner needle 110 is shown in FIG. 20. The diameter of inner needle 110 is 0.7176 mm, the total length of inner needle 110 is 26.796 mm, and the groove on the needle is 0.4784 mm deep and 1.576 mm long. After inner needle 110 inserts into the skin surface, the skin will expand into the groove and surround the needle.

Inner needle can comprise a generally elongated cylindrical shape having a head portion and a shank portion, wherein the shank portion includes a recessed pocket portion or groove formed in the shank portion. The recessed pocket portion is sized to retain the tissue biopsy sample therein. It should be appreciated that alternative cross-sectional shapes, such as square, can be used.

Outer Needle 112

Figure 21:
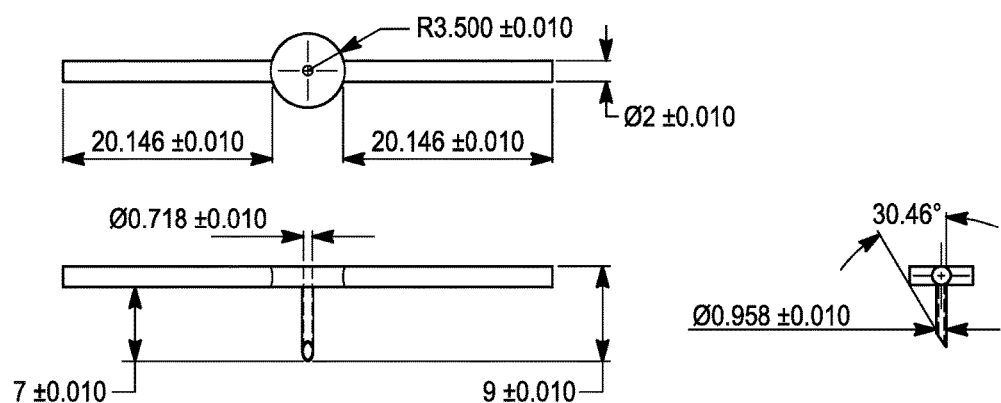
FIG. 21 is a detailed view of the outer needle of the biopsy tissue device according to principles of the present teachings.
Figure 21:
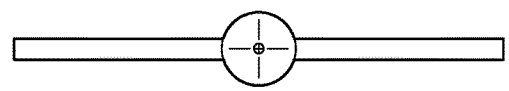

The dimension of outer needle 112 is shown in FIG. 21. The inner diameter is 0.7176 mm and the outer diameter is 0.9576 mm, the total length of outer needle 112 is 9 mm. The cylindrical plate or outer flange 150 on top of outer needle 112 has a diameter of 7 mm and thickness of 2 mm. After inner needle 110 inserts into the skin, outer needle 112 will cut through the skin. Therefore, a small piece of skin sample will be left between inner needle 110 and outer needle 112.

Material List

With all the components determined, a list of all the parts is shown in Table 8. This list includes the part number, part name, quantity, material, size, mass, manufacture process, function and cost. It should be understood, however, that the present material list represents merely one embodiment of the present teachings and variations and modification are anticipated (e.g. size, shape, material type, color, finish, and the like). The material list merely represents an exemplary configuration.

TABLE 8

Material list

| Part # | Part Name | Qty | Material | Color/finish | Size (mm) | Mass (g) | Function |
|---|---|---|---|---|---|---|---|
| 1 | Housing | 1 | ABS Plastic | White | 13 × 130 | 12.17 | Hold the needles |
| 2 | Upper trigger latch 120 | 1 | ABS Plastic | White | 25 × 4 × 1.5 | 3.59 | Control inner needle |
| 3 | Inner Needle | 1 | Stainless Steel | silver | / | 0.08 | Insert into skin |
| 4 | Outer Needle | 1 | Stainless Steel | silver | / | 1.10 | Cut through skin |
| 5 | Screw (91800A087) | 4 | Stainless Steel | grey | 2.3 × 10 | 0.09 | Fasten housing |
| 6 | Nut (91828A004) | 4 | Stainless Steel | grey | 3 × 1 | 0.053 | Fasten housing |
| 7 | Spring 1 (9434K36) | 1 | Music wire | silver | 6.1 × 9.5 | 0.162 | Push outer needle |
| 8 | Spring 2 (9434K43) | 1 | Music wire | silver | 6.1 × 15.9 | 0.598 | Push inner needle |
| 9 | molding | 1 | ABS plastic | white | / | / | Store sample |
| 10 | casing | 1 | ABS plastic | white | / | / | |
| 11 | Precision Miniature Stainless Steel Welded & Drawn Tubing (89935K231) | 1 | 316 Stainless steel | silver | 20 Gauge | / | Cut tissue |
| 12 | Super Corrosion Resistant Stainless Steel (89325K13) | 1 | Stainless steel | silver | 5/16" Diameter, 6' Length Rod | / | Move outer needle 112 |
| 13 | Stainless Steel 316 LVM wire | 1 | Stainless steel | silver | 0.027" Diameter, 60" Length | / | Hold the tissue |

According to the principles of the present teachings, there are several unique functional features of the proposed skin tissue biopsy device:
i) Extracts tissues from a relatively small depth (<5 mm, typically 2 mm), most other biopsy devices extract tissues from much deeper;
ii) Does the above in a minimally invasive manner (existing skin biopsy devices cause considerable pain and leave a large exposed cut, left to heal over time);
iii) Biopsy device 100 offers a single step operation. The healthcare provider (nurse or doctor) presses a single button to carry out the entire process. There are no careful adjustments to make or complicated procedure to follow; and iv) Purely mechanical construction, minimal part counts, and low-cost.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A tissue biopsy device for extracting a tissue biopsy sample from a patient, said tissue biopsy device comprising:
    a housing;
    an inner needle assembly slidably disposed within said housing between a first retained position and a first deployed position, the inner needle assembly being completely contained within the housing in the first retracted position, said inner needle assembly being biased in said first deployed position by a first spring member, said inner needle assembly puncturing the tissue of the patient in said first deployed position;
    a trigger latch being a flexural member, the trigger latch selectively retaining said inner needle assembly in the first retained position opposite said first deployed position against said biasing of said first spring member, said trigger latch being operable to release said inner needle assembly from said first retained position to said first deployed position;
    an outer needle assembly slidably disposed within said housing between a second retained position and a second deployed position, the outer needle assembly being completely contained within the housing in the second retracted position, said outer needle assembly being biased in said second deployed position by a second spring member, said outer needle assembly cutting the tissue of the patient in said second deployed position;
    a retaining latch selectively retaining said outer needle assembly in said second retained position opposite said second deployed position against said biasing of said second spring member, said retaining latch being configured to automatically release said outer needle assembly from said second retained position to said second deployed position solely in response to said release of said inner needle assembly from said first retained position to said first deployed position,
    wherein said inner needle assembly is slidably disposed within said outer needle assembly such that an inner needle of said inner needle assembly is slidably and coaxially contained within an outer needle of said outer needle assembly, said inner needle comprises a generally elongated cylindrical shape defining a head portion and a shank portion, said shank portion having a recessed pocket portion formed therein, said recessed pocket portion being sized to retain the tissue biopsy sample therein, said outer needle selectively retains the tissue biopsy sample within the recessed pocket portion of said inner needle; and
    a retraction handle extending from the outer needle assembly and configured to retract said outer needle assembly and be rotated into engagement with a retaining slot formed in the housing to reveal the tissue biopsy sample within the recessed pocket portion of said inner needle while said inner needle assembly remains in said first deployed position.

2. The tissue biopsy device according to claim 1 wherein said trigger latch comprises an elongated beam.

3. The tissue biopsy device according to claim 1 wherein said trigger latch comprises a living hinge.

4. The tissue biopsy device according to claim 1 wherein lengths of said inner needle and said outer needle are configured to extract the tissue biopsy sample from a shallow skin depth of less than 5 millimeters.

5. The tissue biopsy device according to claim 1 wherein the trigger latch is integrally formed with the inner needle assembly for movement therewith.

6. A tissue biopsy device for extracting a tissue biopsy sample from a patient, said tissue biopsy device comprising:
    a housing;
    an inner needle assembly slidably disposed within said housing between a first retained position and a first deployed position, the inner needle assembly being completely contained within the housing in the first retracted position, said inner needle assembly being biased in said first deployed position by a first spring member, said inner needle assembly having an inner cylinder and an inner needle coupled thereto for puncturing the tissue of the patient in said first deployed position;
    a trigger latch being a flexural member, the trigger latch selectively retaining said inner needle assembly in said first retained position opposite said first deployed position against said biasing of said first spring member, said trigger latch being operable to release said inner needle assembly from said first retained position to said first deployed position in response to flexural articulation of a button member by a user;
    an outer needle assembly slidably disposed within said housing or said inner cylinder between a second retained position and a second deployed position, the outer needle assembly being completely contained within the housing in the second retracted position, said outer needle assembly being biased in said second deployed position by a second spring member, said outer needle assembly having an outer needle defining a central bore slidably receiving said inner needle therein in a coaxial orientation, said outer needle having a distal tip for cutting the tissue of the patient in said second deployed position;
    a retaining latch selectively retaining said outer needle assembly in said second retained position opposite said second deployed position against said biasing of said second spring member, said retaining latch being configured to automatically release said outer needle assembly from said second retained position to said second deployed position solely in response to said release of said inner needle assembly from said first retained position to said first deployed position,
    wherein said inner needle comprises a generally elongated cylindrical shape defining a head portion and a shank portion, said shank portion having a recessed pocket portion formed therein, said recessed pocket portion being sized to retain the tissue biopsy sample therein, said outer needle selectively retains the tissue biopsy sample within the recessed pocket portion of said inner needle; and
    a retraction handle extending from the outer needle assembly and configured to retract said outer needle assembly and be rotated into engagement with a retaining slot formed in the housing to reveal the tissue biopsy sample within the recessed pocket portion of said inner needle while said inner needle assembly remains in said first deployed position.

7. The tissue biopsy device according to claim 6 wherein said trigger latch comprises an elongated flexure beam.

8. The tissue biopsy device according to claim 6 wherein said trigger latch comprises a living hinge.

9. The tissue biopsy device according to claim 6 wherein lengths of said inner needle and said outer needle are configured to extract the tissue biopsy sample from a shallow skin depth of less than 5 millimeters.

10. The tissue biopsy device according to claim 6 wherein the trigger latch is integrally formed with the inner needle assembly for movement therewith.

* * * * *